(12) United States Patent
Ato

(10) Patent No.: US 11,944,349 B2
(45) Date of Patent: Apr. 2, 2024

(54) ADJUSTABLE VASCULAR CLOSURE DEVICE ASSEMBLY

(71) Applicant: TERUMO MEDICAL CORPORATION, Somerset, NJ (US)

(72) Inventor: Masanori Ato, Wilmington, DE (US)

(73) Assignee: TERUMO MEDICAL CORPORATION, Somerset, NJ (US)

( * ) Notice: Subject to any disclaimer, the term of this patent is extended or adjusted under 35 U.S.C. 154(b) by 59 days.

(21) Appl. No.: 17/679,762

(22) Filed: Feb. 24, 2022

(65) Prior Publication Data

US 2022/0265318 A1 Aug. 25, 2022

Related U.S. Application Data

(60) Provisional application No. 63/153,860, filed on Feb. 25, 2021.

(51) Int. Cl.
  *A61B 17/34* (2006.01)
  *A61B 17/00* (2006.01)
  *A61B 17/12* (2006.01)

(52) U.S. Cl.
  CPC ...... *A61B 17/3496* (2013.01); *A61B 17/0057* (2013.01); *A61B 2017/00778* (2013.01); *A61B 2017/12004* (2013.01)

(58) Field of Classification Search
  CPC ............ A61B 17/0057; A61B 17/3496; A61B 2017/00367; A61B 2017/00659; A61B 2017/00778; A61B 2017/12004
  See application file for complete search history.

(56) References Cited

U.S. PATENT DOCUMENTS

| 4,826,490 A | 5/1989 | Byrne et al. |
| 4,850,960 A | 7/1989 | Grayzel |

(Continued)

FOREIGN PATENT DOCUMENTS

| WO | WO-2012/135761 A1 | 10/2012 |
| WO | WO-2013/188351 A2 | 12/2013 |

OTHER PUBLICATIONS

International Search Report and Written Opinion in PCT Appl. No. PCT/US2022/017693, dated Jun. 20, 2022.

(Continued)

*Primary Examiner* — Mohamed G Gabr
(74) *Attorney, Agent, or Firm* — Foley & Lardner LLP

(57) ABSTRACT

A vascular closure device assembly, comprises a sheath comprising: a sheath main body defining a channel therethrough, a sheath engagement portion, and a sheath mounting portion located at a proximal end of the sheath main body. The assembly comprises a housing within which the sheath mounting portion is secured such that the sheath is rotatable relative to the housing, and such that the housing inhibits axial displacement of the sheath relative to the housing. The assembly also includes a dilator comprising a dilator main body, and a dilator engagement portion extending from the dilator main body towards the sheath. The dilator engagement portion is configured to engage the sheath engagement portion such that axial displacement of the dilator relative to the sheath causes the sheath to rotate relative to the housing, and wherein the housing is configured to inhibit axial displacement of the sheath during rotation.

14 Claims, 13 Drawing Sheets

(56) References Cited

U.S. PATENT DOCUMENTS

| | | |
|---|---|---|
| 8,062,316 B2 | 11/2011 | Patel et al. |
| 8,192,402 B2 | 6/2012 | Anderson et al. |
| 9,149,606 B2 | 10/2015 | Beissel et al. |
| 9,839,768 B2 | 12/2017 | Ibragimov |
| 2011/0066181 A1 | 3/2011 | Jenson et al. |
| 2015/0057671 A1 | 2/2015 | Goode et al. |
| 2016/0262862 A1* | 9/2016 | Fischer ............ A61B 17/06109 |

OTHER PUBLICATIONS

International Preliminary Report on Patentability for PCT Appl. No. PCT/US2022/017693, dated Aug. 29, 2023.

* cited by examiner

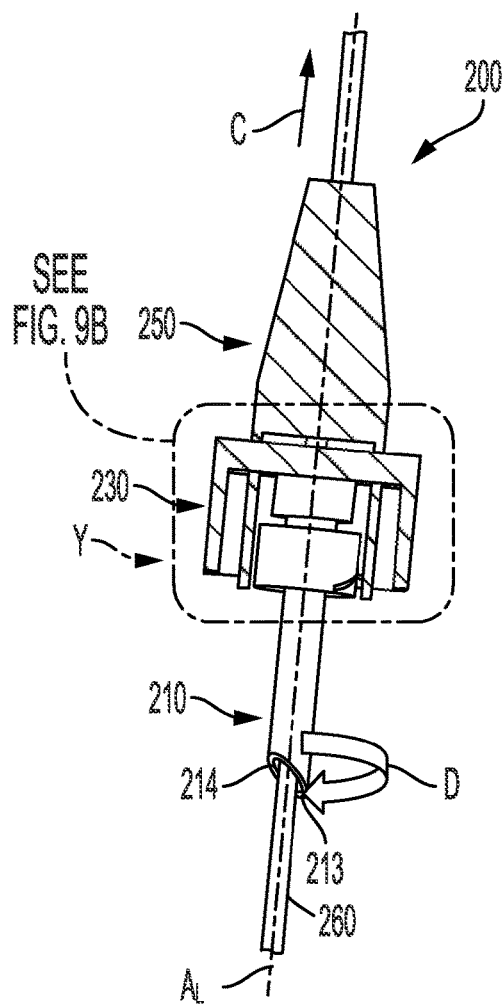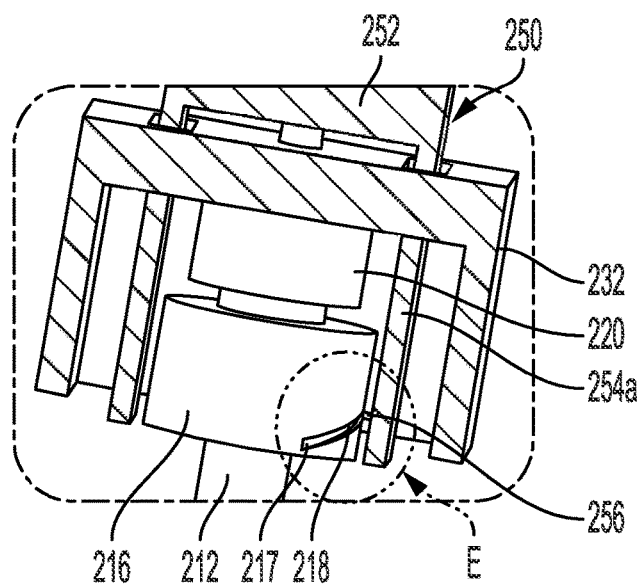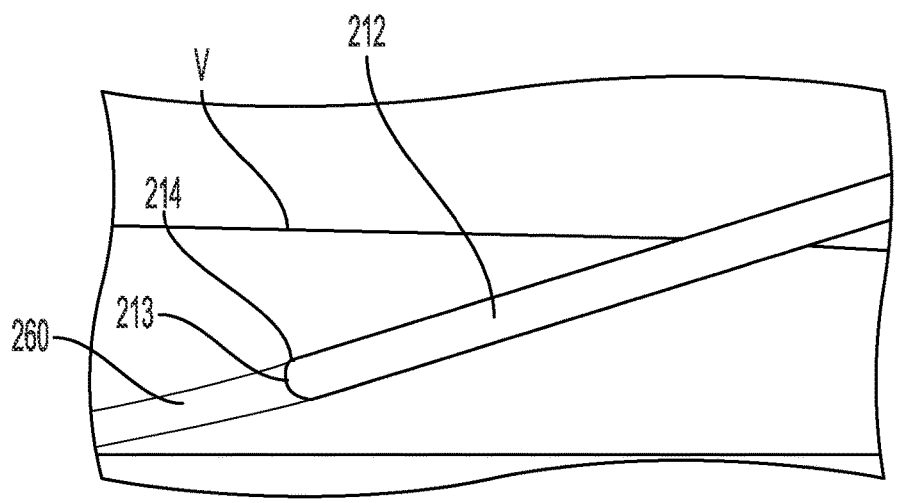
FIG. 9A  FIG. 9B
FIG. 9C

ADJUSTABLE VASCULAR CLOSURE DEVICE ASSEMBLY

CROSS-REFERENCE TO RELATED APPLICATIONS

The present disclosure claims the benefit of and priority to U.S. Provisional Application No. 63/153,860, filed Feb. 25, 2021, the disclosure of which is incorporated herein by reference in its entirety.

TECHNICAL FIELD

The present disclosure relates generally to vascular closure device assemblies that can be adjusted in situ to be in a desired orientation.

BACKGROUND

Vascular trauma such as arterial or venous trauma can result in rapid blood loss, and can prove fatal if blood flow is not stemmed in a rapid fashion by performing vascular hemostasis, i.e., closing and repairing the opening in the vessel from which blood is leaking such that the cardiovascular system can regain its normal function of providing blood to various parts of the body at normal blood pressure. Conventionally, hemostasis is achieved by applying compression at a location of a patient's body over the skin of the patient, but is not very effective in closing the opening and can take a relatively long time in achieving hemostasis, if at all. Recently vascular closure devices ("VCDs") have been used to rapidly achieve hemostasis. Some VCDs include a sheath that is inserted first into a vessel in which hemostasis is being performed. Various components of the VCD are inserted through the sheath towards, or into the vessel, and the sheath may serve to locate various components of the VCD relative to the vessel.

SUMMARY

Embodiments described herein relate generally to systems and methods for obtaining a proper orientation of a sheath relative to a vessel. In particular, embodiments described herein relate to VCD assemblies that include a sheath having a beveled distal end and a proximal end secured to a housing, and a dilator that engages the sheath to move the sheath between a first configuration in which an axis bisecting the beveled distal end and extending through the tip of beveled distal end is at an angle relative the vessel such that the tip of the beveled distal end is inserted into the vessel, and a second configuration in which the sheath rotates while the housing inhibits axial displacement of the sheath such that the bisecting axis is substantially parallel to the vessel.

In some embodiments, a VCD assembly comprises: a sheath comprising: a sheath main body defining a channel therethrough, a sheath engagement portion, and a sheath mounting portion located at a proximal end of the sheath main body; a housing, the sheath mounting portion being secured within the housing such that the sheath is rotatable relative to the housing, and such that the housing inhibits axial displacement of the sheath relative to the housing; and a dilator comprising: a dilator main body, and a dilator engagement portion extending from the dilator main body towards the sheath, wherein the dilator engagement portion configured to engage the sheath engagement portion such that axial displacement of the dilator relative to the sheath causes the sheath to rotate relative to the housing, the housing configured to inhibit axial displacement of the sheath during rotation.

In some embodiments, a method of operating a vascular closure device assembly that comprises a sheath having a sheath main body defining a beveled distal end and a sheath mounting portion located at a proximal end of the sheath main body, a housing within which the sheath mounting portion is disposed, and a dilator engaging the sheath through the housing, the method comprising: inserting at least a portion of the dilator into the housing such that the dilator engages the sheath and moves the sheath into a first configuration in which a tip of the beveled distal end is located on a side corresponding to a side of a vessel in which an opening is located; inserting the sheath into a tissue track in the first configuration; inserting the tip of the beveled distal end of the sheath through the wall of the vessel into the vessel; and displacing the dilator axially away from the housing such that the dilator engages the sheath and causes the sheath to rotate relative to the housing and move into a second configuration in which the tip of the beveled distal end is located on a side opposite the side of the vessel in which the opening is located, the housing inhibiting axial displacement of the sheath relative to the housing.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 9A is a front perspective view of the VCD assembly of FIG. 2 being moved into a second configuration by displacing a dilator away from the housing; FIG. 9B is a cross-sectional view of a portion of the VCD assembly of FIG. 9A shown by the arrow Y in FIG. 9A; and FIG. 9C is a side view of the orientation of a beveled distal end of the sheath within the vessel.

Figure 1:
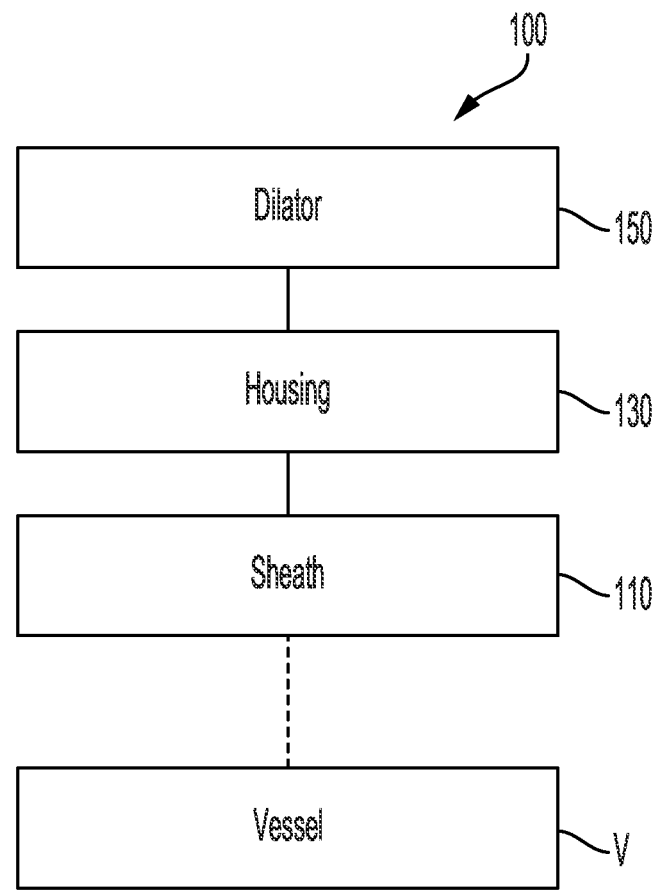
FIG. 1 is a schematic block diagram of a VCD assembly, according to an embodiment.
Figure 2:
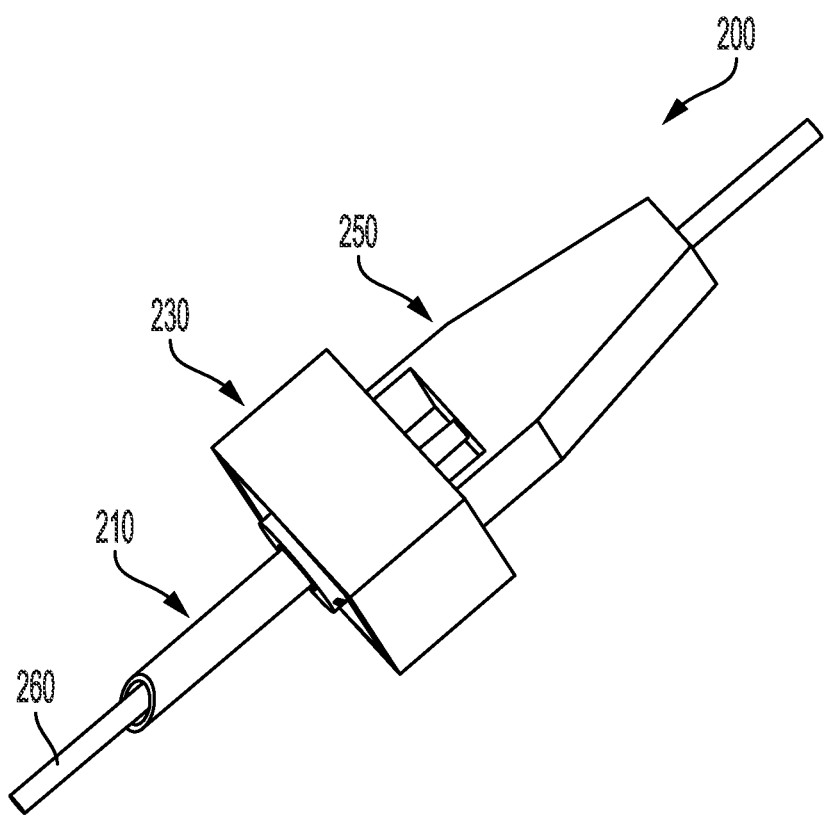
FIG. 2 is a front, right, bottom view of a VCD assembly, according to another embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Embodiments described herein relate generally to systems and methods for obtaining a proper orientation of a sheath relative to a vessel. In particular, embodiments described herein relate to VCD assemblies that include a sheath having a beveled distal end and a proximal end secured to a housing, and a dilator that engages the sheath to move the sheath between a first configuration in which an axis bisecting the beveled distal end and extending through the tip of beveled distal end is at an angle relative the vessel such that the tip of the beveled distal end is inserted into the vessel, and a second configuration in which the sheath rotates while the housing inhibits axial displacement of the sheath such that the bisecting axis is substantially parallel to the vessel.

Some VCDs include a sheath that is inserted first into a vessel on which hemostasis is being performed. Various components of the VCD are inserted through the sheath towards or into the vessel, and the sheath may serve to locate various components of the VCD relative to the vessel. For example, anchors may be inserted through the sheath (e.g., via carrier tubes) into the vessel to facilitate hemostasis or perform other intravascular procedures. It is often desirable for such anchors to be substantially parallel to a wall of the vessel. However, some sheaths have a beveled distal end. Orienting the beveled distal end substantially parallel to wall of the vessel, i.e., in a bevel up position, allows the anchor to also be oriented substantially parallel to the wall of the vessel. However, the parallel orientation of the beveled distal end relative to the wall of the vessel is undesirable for inserting the sheath into the vessel because a large surface area of the beveled distal end comes in contact with the vessel wall, which can increase the required insertion force as well as increase trauma on the vessel.

On the other hand, orienting the beveled distal end at an angle with the respect to the vessel wall, i.e., in a bevel down position, such that a tip contacts the vessel wall first, facilitates insertion. However, in this orientation, the anchor also emerges at an angle with respect to the vessel wall within the vessel, which is undesirable. For example, it may be relatively easy to inadvertently withdraw the anchor from the vessel if the anchor is in the angular position when the sheath is withdrawn from the vessel. Manual rotation of the sheath is complicated and makes it difficult to achieve desired orientation, and also increases the risk of puncturing the opposite side of the vessel wall due to unintended axial displacement.

Various embodiments of the VCD assemblies described herein may provide one or more advantages, including, for example: (1) facilitating insertion of a sheath into a vessel by orienting the sheath in a bevel down position such that a tip of a beveled distal end of the sheath is inserted first through the wall of the vessel; (2) reducing insertion force and trauma into the vessel by allowing insertion in the bevel down position; (3) facilitating reorientation of the beveled distal end into a bevel up position after insertion by simple axial movement of a dilator, which causes angular reorientation of the beveled distal end without causing any significant axial displacement thereof; and (4) allowing an anchor to be oriented substantially parallel to the vessel to facilitate hemostasis.

As described herein the term "proximal end" refers to an end that is proximate to a user of a VCD assembly and the term "distal end" refers to an end that is distal from a user of the VCD assembly and proximate to a subject on which a vascular closure procedure or any other intravascular procedure is being performed via the VCD assembly.

FIG. 1 is a schematic block diagram of VCD assembly 100 (hereinafter "assembly 100"), according to an embodiment. The assembly 100 includes a sheath 110, a housing 130, and a dilator 150. The assembly 100 may be used to perform vascular hemostasis or to perform any other intravascular procedure (e.g., angiography, angioplasty, stent placement, etc.).

The sheath 110 is configured to be inserted through a tissue track into a vessel V (e.g., a vein or an artery). In some embodiments, the sheath 110 includes a sheath main body defining a channel therethrough. The channel is configured to allow passage of various hemostasis components or other intravascular components therethrough. Such components may include, but are not limited to guide wires, carrier tubes, balloon tubes, anchor tubes needles, etc. In some embodiments, the sheath main body includes a beveled distal end that includes a tip and is configured to be inserted into the vessel V. As previously described, it may be desirable to orient the beveled distal end at an angle with respect to a vessel wall such that a tip of the beveled distal end contacts and is inserted through the vessel wall.

The sheath 110 may include a sheath mounting portion located at a proximal end of the sheath main body. The sheath mounting portion may be disposed in the housing 130 such that the sheath mounting portion is rotatable relative to the housing 130, and such that the housing 130 inhibits axial displacement of the sheath relative to the housing 130. For example, the housing 130 may include a mounting structure defined within the housing 130, and the sheath mounting portion is disposed within the mounting structure. In some embodiments, the sheath mounting portion is cylindrical and may have a diameter that is larger than a diameter of the sheath main body. In such embodiments, the mounting structure includes a cylindrical wall extending away from a proximal wall of the housing 130 that is located proximate to the dilator 150, towards the sheath 110. A ledge may extend radially inwards from a distal rim of the cylindrical wall. The sheath mounting portion may have an axial length corresponding to an axial length of the cylindrical wall such that the mounting portion is secured between an axially distal surface of the proximal wall of the housing 130 and a proximal surface of the ledge so as to inhibit axial displacement while allowing rotation of the sheath 110 relative to the housing 130.

In some embodiments, the sheath 110 may include a sheath engagement portion configured to be engaged by the dilator 150. In some embodiments, the dilator 150 may include a dilator main body, and dilator engagement portion extending from the dilator main body towards the sheath 110. The dilator engagement portion is configured to engage the sheath engagement portion such that axial displacement of the dilator 150 relative to the sheath 110 causes the sheath to rotate relative to the housing 130, while the housing is configured to inhibit axial displacement of the sheath 110.

For example, the dilator 150 may be configured to move the assembly 100 between a first configuration and a second configuration. In the first configuration, the dilator main body is proximate to the sheath 110 and the dilator engagement portion engages the sheath engagement portion at a first position, and the tip of beveled distal end is located in a first rotational position, for example, in which the tip of the beveled distal end is located on a side corresponding to a side of the vessel V in which an opening defined in the vessel V is located. Moreover, in the first configuration, a bisecting axis that bisects the beveled distal end and extends through the tip is oriented at an angle with respect to the vessel. Thus, in the first configuration the sheath 110 is oriented such that a tip of the beveled distal end of the sheath 110 is located proximate to the vessel V so as to enter the vessel first as the assembly 100 is displaced axially towards the vessel V. This facilitates insertion of the beveled distal end of the sheath 110 into the vessel V.

In the second configuration, the dilator engagement portion engages the sheath engagement portion at a second position that is proximal the first position, and the tip of the beveled distal end is located in a second rotational position that is rotationally offset from the first rotational position. Expanding further, the dilator main body is moved axially away from the sheath 110 such that the dilator 150 engages causing the sheath 110 to rotate relative to the housing 130 such that the tip of the beveled distal end is located on a side opposite the side of the vessel V in which the opening is located. The housing 130 inhibits axial displacement of the sheath 110 relative to the housing 130. In the second configuration, the bisecting axis can be substantially parallel to the vessel V, for example, a wall of the vessel V through which the sheath 110 is inserted. As described herein, the term "substantially parallel" with reference to the bisecting axis implies that the bisecting axis and thereby, an end surface of the sheath 110 formed by the beveled distal end is oriented at an angle within a range of ±10 degrees with respect to the vessel V. The rotation may be performed after the beveled distal end is inserted through the vessel wall into the vessel. The bisecting axis and thereby, the beveled distal end of the sheath 110 being substantially parallel to the vessel wall facilitates orienting an anchor communicated through the channel defined by the sheath 110 into the vessel V in a desired orientation, for example, substantially parallel to the vessel wall. In some embodiments, the sheath 110 is rotatable by an angle of about 180 degrees (e.g., in a range of 160 degrees to 200 degrees, inclusive) between the first configuration and the second configuration, such that the second rotational position is rotationally offset from the first rotational position by about 180 degrees.

In some embodiments, the dilator engagement portion includes one or more dilator arms (e.g., 1, 2, 3, 4, or more dilator arms) extending from the dilator 150 towards the sheath 110. In such embodiments, the housing 130 defines one or more slots corresponding to the number of dilator arms. Each of the one or more dilator arms may extend through a corresponding slot of the one or more slots towards the sheath engagement portion, for example, to engage the sheath engagement portion for moving the assembly between the first and second configuration, as previously described. In other embodiments, the dilator 150 may include any other structures for engaging the sheath 110 and the dilator arms may be excluded.

The dilator engagement portion may include any suitable structures for engaging the sheath 110 so as to cause rotation of the sheath 110 as the dilator main body is axially displaced relative the housing 130. Such structures may include, for example, protrusions defined on one or more of the dilator arms, lead screws, cams, gears, threads, etc. In some embodiments, the sheath engagement portion defines a groove, for example, a helical groove. For example, the sheath engagement portion may include a cylindrical structure disposed between the beveled distal end and the sheath mounting portion and may have a larger diameter than at least the sheath main body, and in some embodiments, the sheath mounting portion. In some embodiments, at least a portion of the sheath engagement portion may be disposed within the housing 130. The groove may be defined on an outer surface of the sheath engagement portion. In such embodiments the dilator engagement portion may include an engagement member (e.g., a protrusion or a pin) protruding from a corresponding dilator arm of the one or more dilator arms into the groove.

In the first configuration, the engagement member is located at a distal end of the groove. As the dilator 150 is moved axially away from the housing 130, the axial movement causes the engagement member to engage the groove, for example, slide along or ride along the groove. Since the housing 130 inhibits axial displacement of the sheath 110, the engagement member causes the sheath engagement portion and thereby, the sheath 110 to rotate relative to the housing 130 until the engagement member is located at a proximal end of the groove and the assembly 100 is in the second configuration via rotation of the sheath 110, for example, by an angle of about 180 degrees.

In some embodiments, the proximal end of the groove is structured such that axial displacement of the dilator 150 away from the housing 130 once the assembly 100 is in the second configuration causes the engagement member to disengage from the groove to allow the dilator 150 to be removed from the assembly 100. For example, the proximal end of the groove may form a ramp to allow the engagement member to slide out of the groove. In other embodiments, a vertical channel may be defined on an outer surface of the sheath engagement portion from a proximal edge of the sheath engagement portion to the proximal end of the groove. Axial displacement of the dilator 150 away from the sheath 110 once the engagement member is at the proximal end may cause the engagement member to slide into the vertical channel and ultimately out of the vertical channel such that the engagement member and hence, the dilator engagement portion is disengaged from the sheath engagement portion allowing the dilator 150 to be removed from the assembly 100.

In some embodiments, the dilator 150 may include an inner elongated member extending axially away from the dilator main body towards the sheath 110 and removably disposed through the channel defined through the sheath 110. The inner elongated member may serve to axially align the dilator 150 with respect to the sheath 110 and inhibit lateral movement of dilator 150 relative to the sheath 110. In such embodiments, the housing 130 may define an aperture through the proximal wall of the housing located proximate to the dilator 150. The inner elongated member may be removably disposed through the aperture into the channel defined by the sheath 110. In some embodiments, the inner elongated member may define a channel therethrough through which a fluid (e.g., saline or drug solution) may be inserted to dilate the vessel V. In some embodiments, a guide wire may be inserted into the vessel V through the sheath 110, and the inner elongated member may be inserted through the sheath 110 along the guide wire.

Referring to FIGS. 2-11, various views of a VCD assembly 200 (hereinafter "assembly 200") are shown, according to an embodiment. The assembly 200 includes a sheath 210, a housing 230, and a dilator 250. The assembly 200 can incorporate features of the assembly 100 described with reference to FIG. 1. The assembly 200 may be used to perform vascular hemostasis or to perform any other intravascular procedure (e.g., angioplasty, stent placement, etc.).

Figure 3:
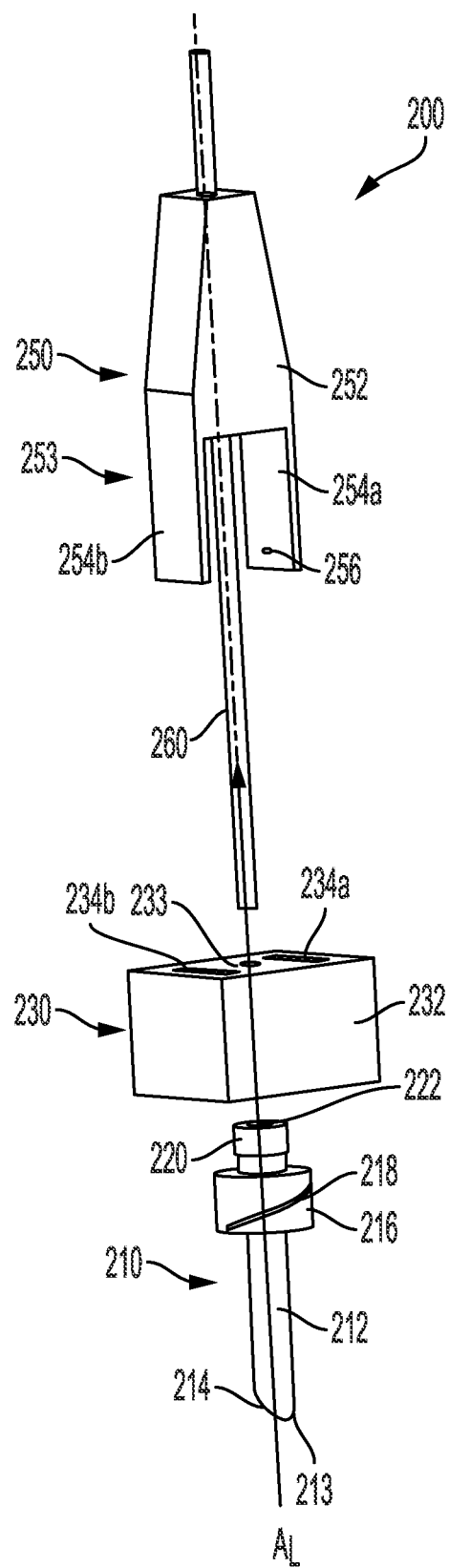
FIG. 3 is an exploded view of the VCD assembly of FIG. 2.
Figure 4A:
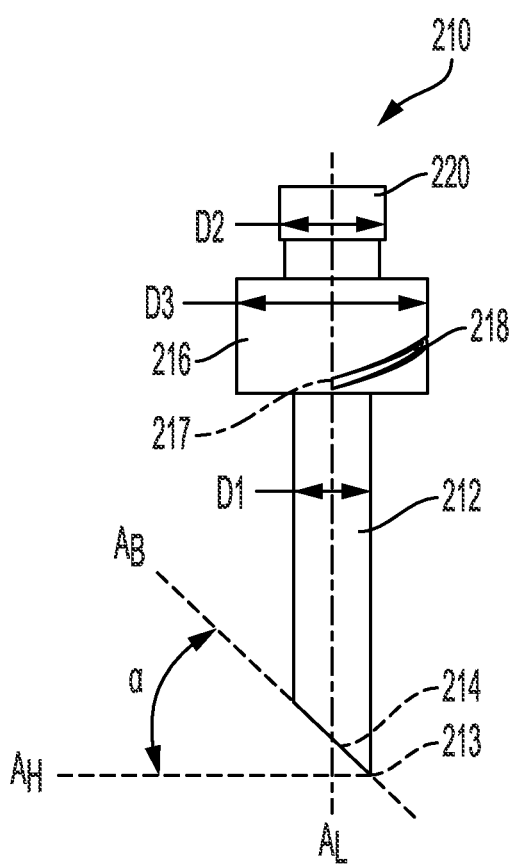
FIG. 4A is right side elevation view.
Figure 4B:
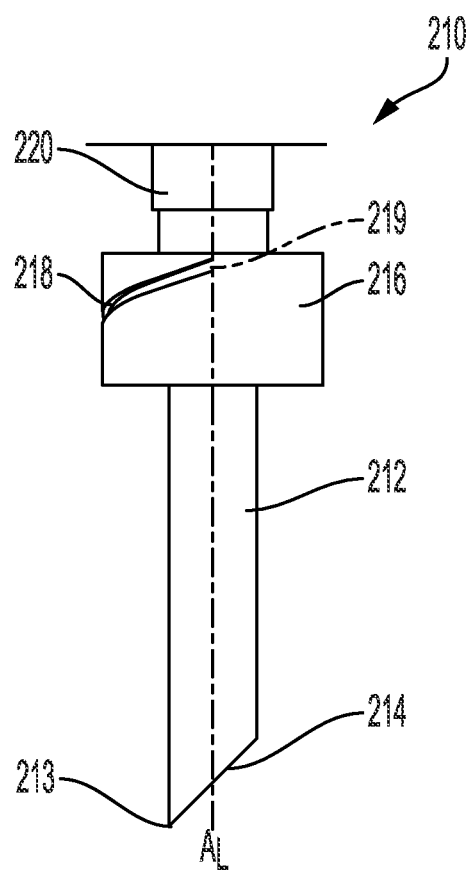
FIG. 4B is a left side elevation view of a sheath included in the VCD assembly of FIG. 2

As shown in FIGS. 3 and 4A-4B, the sheath 210 includes a sheath main body 212, which may be a cylindrical tube-like structure defining a channel 222 therethrough. The sheath 210 is configured to be inserted through a tissue track into a vessel (e.g., the vessel V such as an artery or a vein). The channel 222 is configured to allow passage of various hemostasis components or other intravascular components therethrough (e.g., guide wires, carrier tubes, balloon tubes, anchor tubes, needles, etc.) into the vessel. The sheath main body 212 includes a beveled distal end 214 forming a tip 213. The beveled distal end 214 is configured to be inserted into the vessel. As previously described, it may be desirable to orient the beveled distal end 214 at an angle to a wall of the vessel such that the tip 213 of the beveled distal end 214 contacts, and is inserted through the vessel wall first. In some embodiments, the beveled distal end 214 may define an angle α (e.g., in a range of 30 degrees to 60 degrees, inclusive) with respect to a horizontal axis $A_H$ that is perpendicular to a vertical axis $A_L$ of the assembly 200 and a bisecting axis $A_B$ that bisects the beveled distal end and extends through the tip 213.

The sheath 210 includes a sheath mounting portion 220 located at a proximal end of the sheath main body 212. The sheath mounting portion 220 can be disposed in the housing 230 such that the sheath mounting portion 220 is rotatable relative to the housing 230, and such that the housing 230 inhibits axial displacement of the sheath 210 relative to the housing 230. The sheath main body 212 may have a first diameter D1 and the sheath mounting portion 220 may have a second diameter D2 larger than the first diameter D1. The sheath main body 212 can include a central portion 226 sized to be positioned inward from the sheath engagement portion 216 and distal from the sheath mounting portion 220; as shown in FIG. 6 the central portion 226 can have a larger diameter than the first diameter D1 of the sheath main body 212.

Figure 5A:
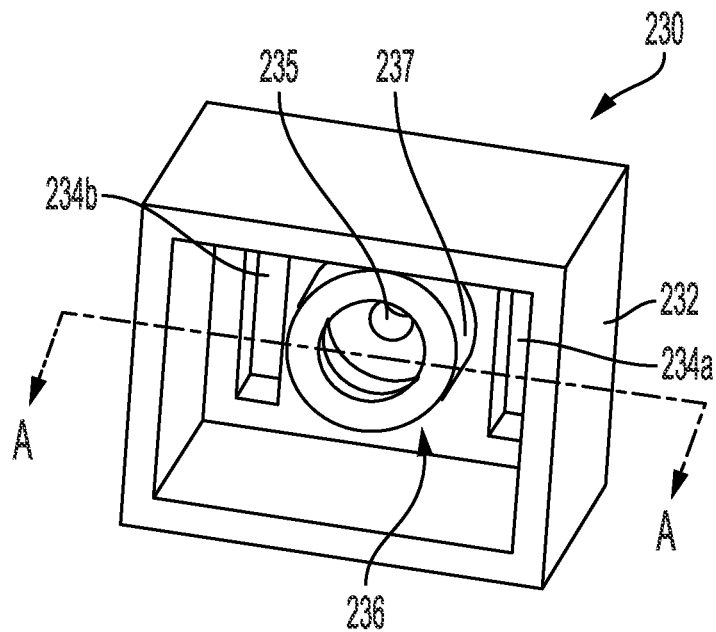
FIG. 5A is front, right, bottom of a housing included in the VCD assembly of FIG. 2, according to an embodiment.
Figure 5B:
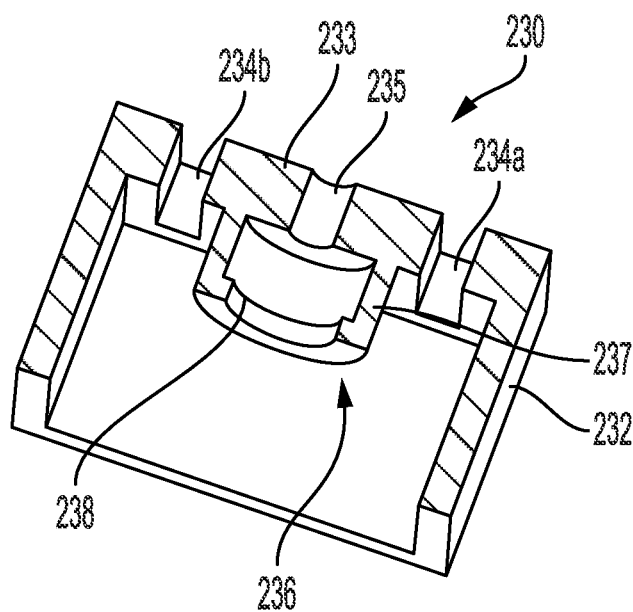
FIG. 5B is a cross-sectional view of the housing of FIG. 5A taken along the line A-A in FIG. 5A.
Figure 6:
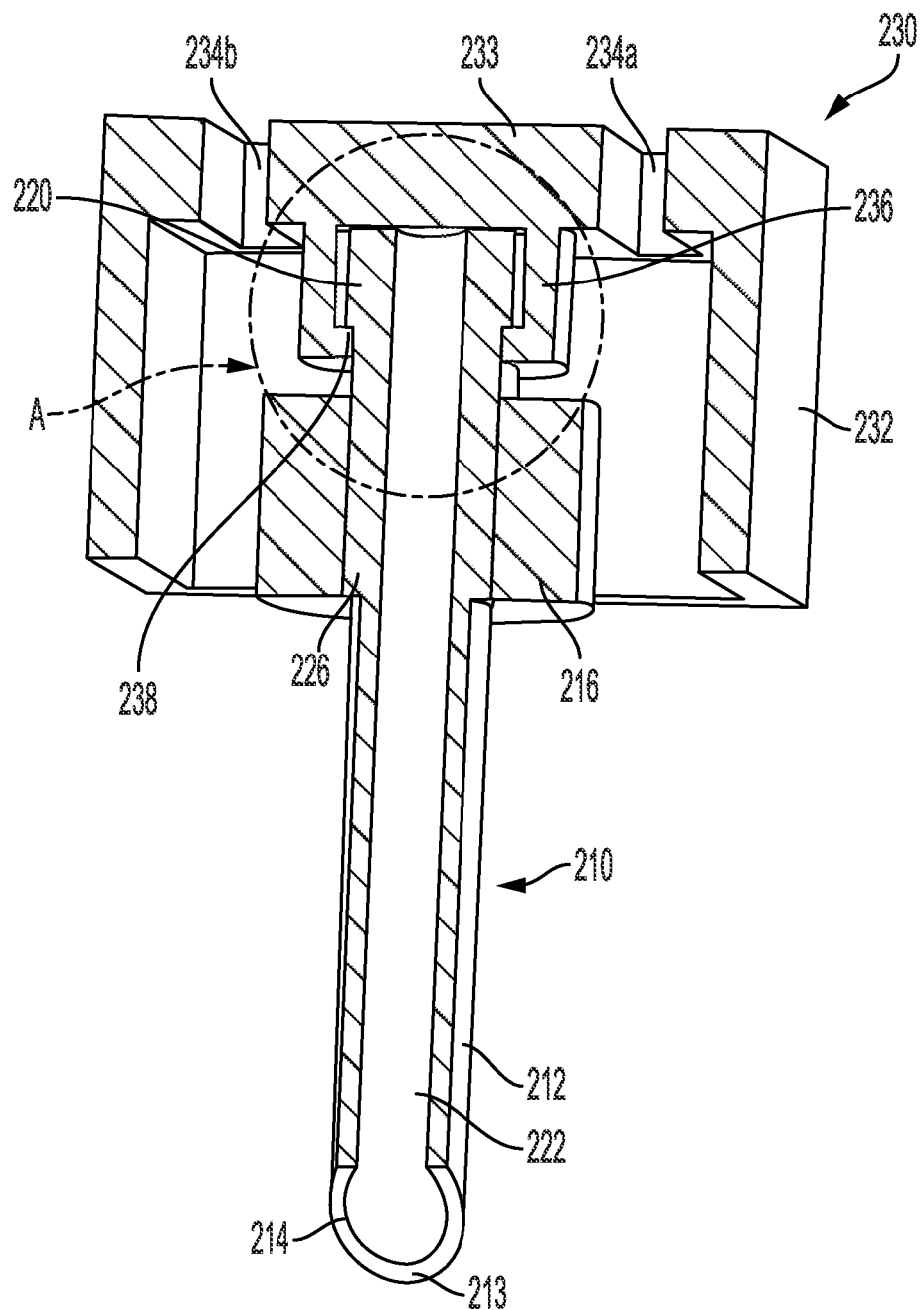
FIG. 6 is another cross-section view of the housing of FIGS. 5A-5B showing a sheath mounting portion of the sheath disposed in a mounting structure of the housing, according to an embodiment.

Expanding further, as shown in FIGS. 5A-6, the housing 230 includes a housing main body 232 that is open at a first end that is distal from the dilator 250, and includes a proximal wall 233 at a second end that is opposite the first end and is proximate to the dilator 250 relative to the first end. The housing main body 232 defines an internal volume within which a mounting structure 236 is disposed at a location indicated by the arrow A. The mounting structure 236 includes a cylindrical wall 237 extending from the proximal wall 233 towards the sheath 210. A ledge 238 extends radially inwards from a distal rim of the cylindrical wall 237 such that an opening is defined at an end of the mounting structure 236 opposite the proximal wall 233. In some embodiments, the opening may have a diameter corresponding the first diameter D1 of the sheath main body 212.

As shown in FIG. 6, the sheath mounting portion 220 is disposed within the mounting structure 236 and the sheath main body 212 is disposed through the opening and extends axially away from the housing 230. The sheath mounting portion 220 may have an axial length corresponding to an axial length of the cylindrical wall 237 (i.e., corresponding to a distance between the proximal wall 233 and the ledge 238) and the diameter D2 can be greater than an inner diameter of the ledge 238, such that the sheath mounting portion 220 is secured between a distal surface of the proximal wall 233 and a proximal surface of the ledge 238. In this manner, the mounting structure 236 inhibits axial displacement of the sheath 210 relative to the housing 230 while allowing rotation of the sheath 210 relative to the housing 230.

The sheath 210 also includes a sheath engagement portion 216 configured to be engaged by the dilator 250, as described in further detail herein. The sheath engagement portion 216 defines a helical groove 218 having a distal end 217 and a proximal end 219. As shown in FIGS. 4A-4B, the sheath engagement portion 216 includes a cylindrical structure disposed between the beveled distal end 214 and the sheath mounting portion 220. The sheath engagement portion 216 has a third diameter D3 larger than the second diameter D2. At least a portion of the sheath engagement portion 216 may be disposed within the housing 230. The helical groove 218 may be defined on an outer surface of the sheath engagement portion 216.

Figure 7:
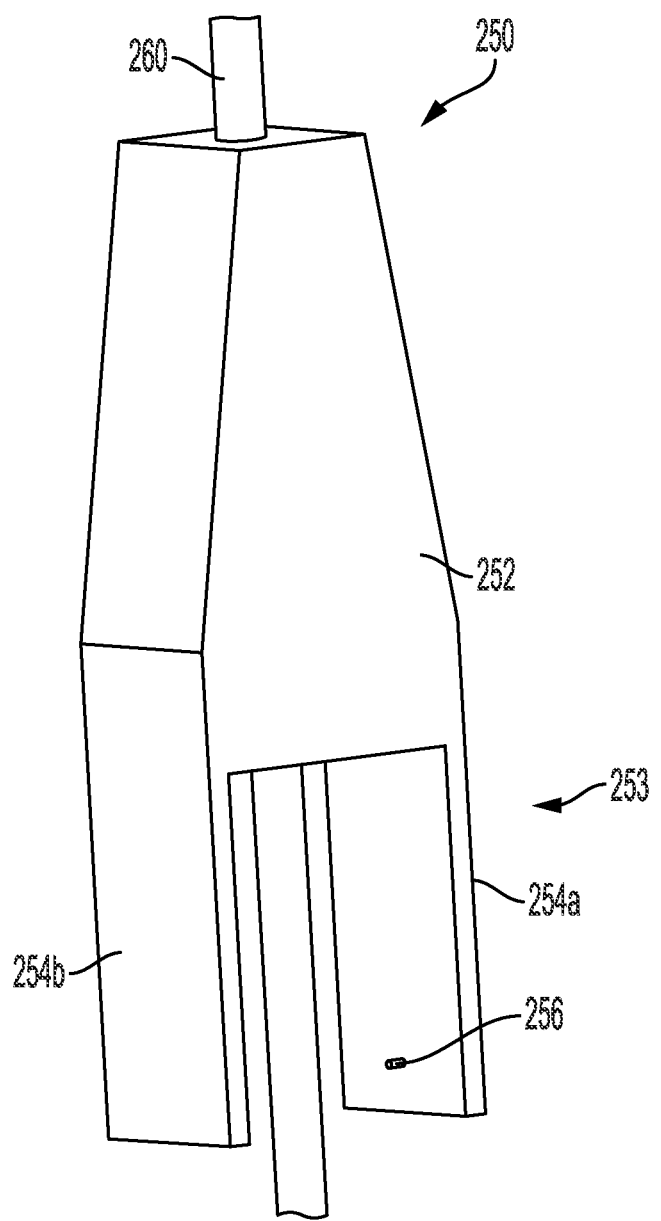
FIG. 7 is a front, left, top perspective view of a dilator included in the VCD assembly of FIG. 2.

As shown in FIG. 7, the dilator 250 may include a dilator main body 252, and a dilator engagement portion 253 extending from the dilator main body 252 towards the sheath 210. In some embodiments, the dilator 250 may include an inner elongated member 260 extending axially away from the dilator main body 252 towards the sheath 210 and removably disposed through the channel 222 defined through the sheath 210. The inner elongated member 260 may serve to axially align the dilator 250 with respect to the sheath 210 and inhibit lateral movement of dilator 250 relative to the sheath 210 and/or to allow insertion of dilating fluids into the vessel through a channel defined through the inner elongated member 260. In some embodiments, the assembly 200 may include a guide wire (not shown) that is inserted into through the channel 222 defined by the sheath 210 into the vessel (e.g., prior to inserting the sheath 210 into the vessel), and the inner elongated member 260 guided along the guide wire through the sheath 210. For example, the inner elongated member 260 may be hollow such that the inner elongated member 260 can be inserted over the guide wire into the sheath 210.

As shown in FIGS. 5A-5B, the housing 230 defines an aperture 235 through the proximal wall 233 of the housing 230 within the mounting structure 236. The inner elongated member 260 can be removably disposed through the aperture 235 into the channel 222 defined by the sheath 210, and may have a length longer than a length of the sheath main body 212 such that a distal end of the inner elongated member 260 protrudes through the beveled distal end 214 of the sheath 210.

The dilator engagement portion 253 is configured to engage the sheath engagement portion 216 such that axial displacement of the dilator 250 relative to the housing 230 causes the sheath 210 to rotate relative to the housing 230, while the housing 230 inhibits axial displacement of the sheath 210. The dilator engagement portion 253 includes a first dilator arm 254a and a second dilator arm 254b extending axially from opposite lateral edges of the dilator main body 252 towards the sheath 210. As shown in FIGS. 5A-6, the proximal wall 233 of the housing 230 defines a first slot 234a and a second slot 234b, which are configured to receive the first dilator arms 254a and the second dilator arm 254b, respectively therethrough. The first dilator arm 254a and the second dilator arm 254b can extend through the first slot 234a and the second slot 234b towards the sheath engagement portion 216.

Figure 8A:
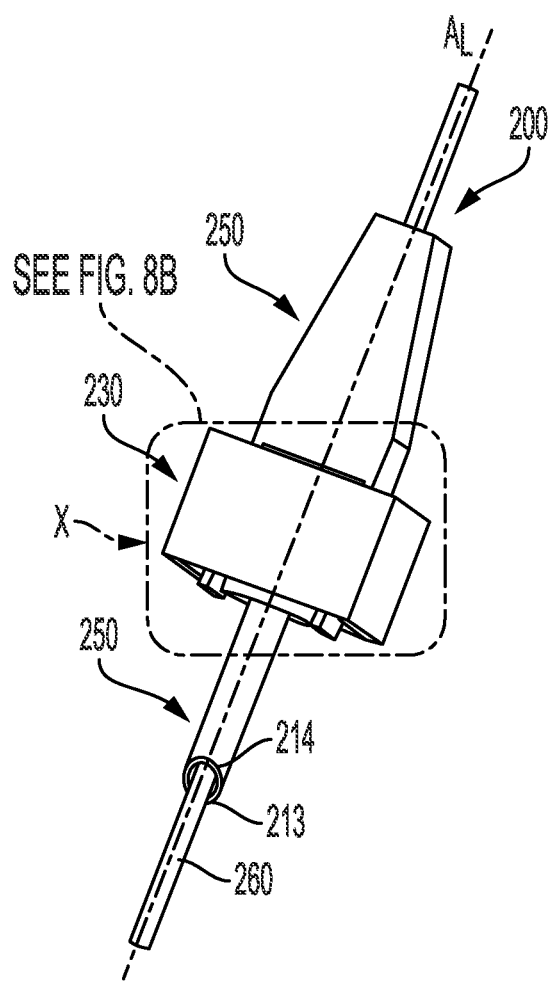
FIG. 8A is a front, right perspective view of the VCD assembly of FIG. 2 in a first configuration.
Figure 8B:
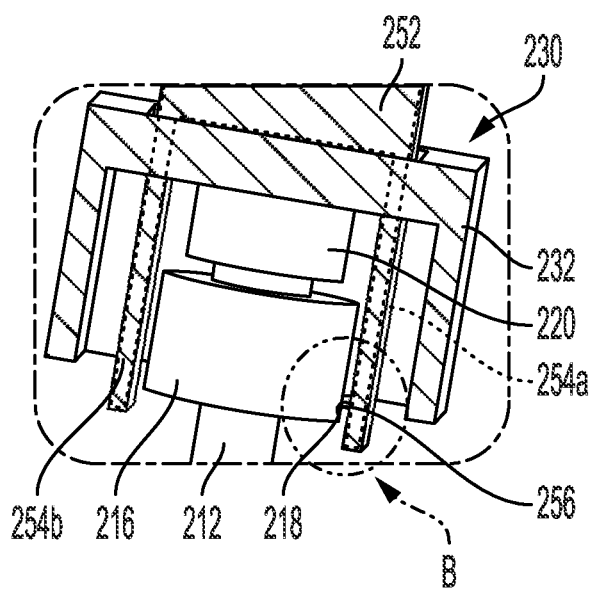
FIG. 8B is a cross-sectional view of a portion of the VCD assembly of FIG. 8A shown by the arrow X in FIG. 8A.

As shown in FIGS. 3 and 7, the dilator engagement portion 253 includes an engagement member 256 (e.g., a protrusion or a pin) protruding from the first dilator arm 254a to be received in the helical groove 218. The engagement member 256 is configured to cause the sheath 210 to rotate as the dilator 250 is axially displaced along the vertical axis $A_L$ (e.g., away from (or towards) the housing 230) by riding along the helical groove 218. FIGS. 3 and 7, among others, show the engagement member 256 as protruding from the first dilator arm 254a (e.g., forming a male portion of an engagement assembly) and the helical groove 218 extending into the sheath engagement portion 216 (e.g., forming a female portion of the engagement assembly); in some embodiments, one or more protruding members can be provided on the sheath engagement member 216 (e.g., to form the male portion of the engagement assembly) and a groove can be provided in one or both dilator arms 254a, 254b. Expanding further, FIGS. 8A-8B show the assembly 200 in a first configuration. In the first configuration, the dilator main body 252 is located axially proximate to the housing 230, and the engagement member 256 is located at the distal end 217 of the helical groove 218, as visible in the portion of the assembly 200 indicated by the arrow B in FIG. 8B, and the beveled distal end 214 is located in a first rotational position.

Figure 8C:
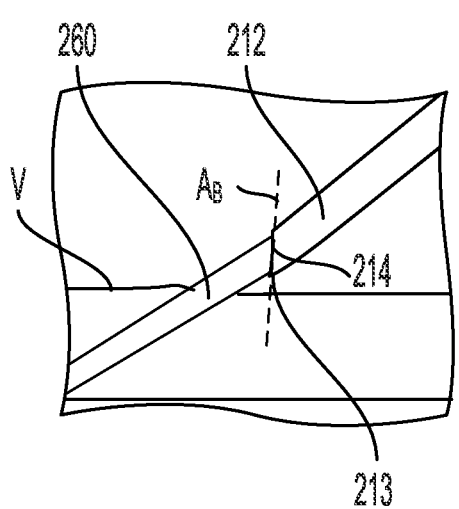
FIG. 8C is a side view of a beveled distal end of the sheath of the VCD assembly of FIG. 8A being inserted into a vessel.
Figure 8D:
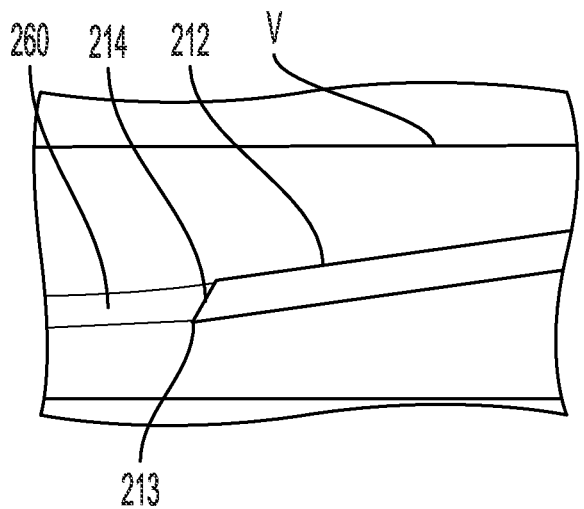
FIG. 8D is a side view of the beveled distal end after being inserted into the vessel.

Moreover, as shown in FIG. 8C, the sheath main body 212 is oriented such that the bisecting axis $A_B$ is oriented at an angle to the vessel V and tip 213 of the beveled distal end 214 of the sheath main body 212 is configured to be located proximate to a vessel V so as to enter the vessel V first as the assembly 200 is displaced axially towards the vessel V as shown in FIG. 8C (e.g., when the sheath 210 is inserted an angle towards the vessel V). This facilitates insertion of the beveled distal end 214 of the sheath 210 into the vessel V while being in the first configuration, as shown in FIG. 8D. In some embodiments, the inner elongated member 260 is inserted first into the vessel V, for example, via an opening formed in the vessel V that is to be closed via the assembly 200 to achieve hemostasis.

To move the assembly 200 into the second configuration, the dilator 250 is moved axially away from the housing 230 in the direction shown by the arrow C in FIG. 9A. For example, a user may hold the housing 230 while pulling the dilator 250 away from the housing 230. As shown in FIGS. 9A-9B, axial displacement of the dilator 250 also displaces the engagement member 256, which is in contact with the helical groove 218, axially away from the beveled distal end 214 of the sheath 210, as visible in the portion of the assembly indicated by the arrow E. However, because the sheath 210 is inhibited from axial translation via the housing 230, the linear force exerted by the engagement member 256 on the helical groove 218 causes the sheath engagement portion 216 and thereby, the sheath 210 to rotate in the direction shown by the arrow D in FIG. 9A. This also causes the beveled distal end 214 of the sheath 210 to rotate, as shown in FIG. 9C (e.g., the beveled distal end 214 has been rotated approximately 90 degrees clockwise relative to the orientation shown in FIG. 8D).

Figure 10A:
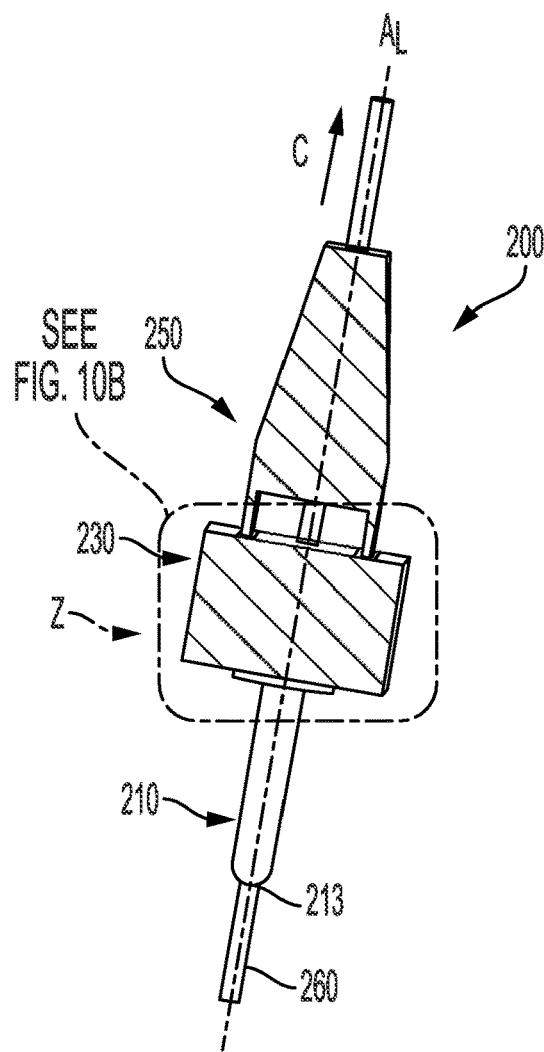
FIG. 10A is a front perspective view of the VCD assembly of FIG. 2 in a second configuration.
Figure 10B:
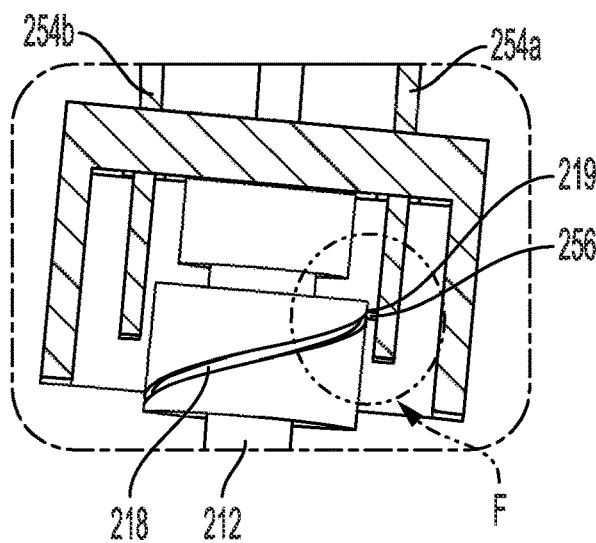
FIG. 10B is a cross-sectional view of a portion of the VCD assembly of FIG. 10A shown by the arrow Z in FIG. 1A.
Figure 10C:
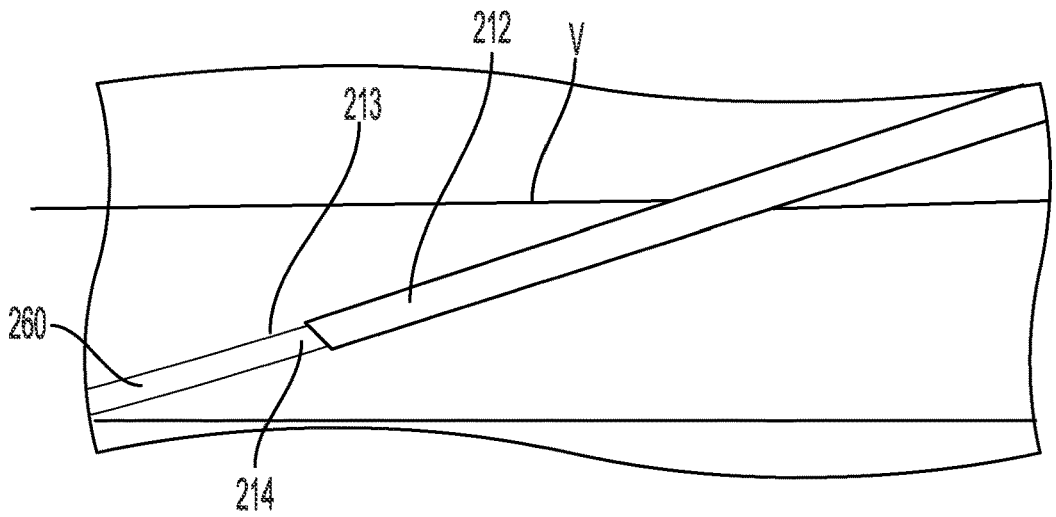
FIG. 10C is a side view of the orientation of a beveled distal end of the sheath within the vessel in the second configuration.

Continued axial displacement of the dilator 250 away from the housing 230 in the direction shown by the arrow C causes the assembly 200 to move into a second configuration, shown in FIG. 10A. In the second configuration, the engagement member 256 is located at the proximal end 219 of the helical groove 218 as visible in the portion of the assembly 200 indicated by the arrow F in FIG. 10B. In the second configuration, as shown in FIG. 10C, the beveled distal end 214 can be rotated by approximately 90 degrees further clockwise than the orientation show in FIG. 9C. For example, in the second configuration the sheath main body 212 can be oriented such that the bisecting axis $A_B$ is the substantially parallel to the vessel and the beveled distal end 214 is, or can be oriented substantially parallel to vessel V (e.g., a proximal vessel wall) without having to further rotate the sheath main body 212. The relative orientation of the bisecting axis $A_B$ and the vessel V can depend, for example, on factors such as a curvature of the vessel V, an angle of the vertical axis $A_L$, and the angle α. The sheath main body 212 is rotated from the first configuration to the second configuration while the beveled distal end 214 is still within the vessel V. In some embodiments, the sheath 210 is rotatable by an angle of about 180 degrees (e.g., in a range of 160 degrees to 200 degrees, inclusive) between the first configuration and the second configuration.

Figure 12A:
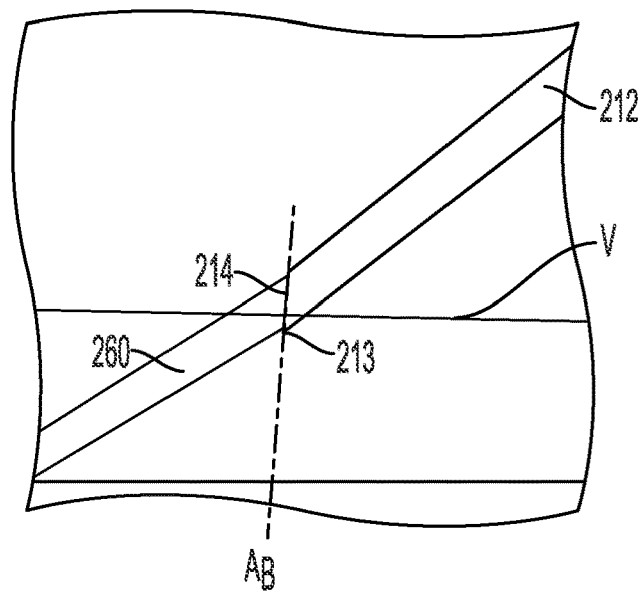
FIG. 12A is a side view of a beveled distal end of the sheath of the VCD assembly of FIG. 2 inserted into a vessel in a first orientation.
Figure 12B:
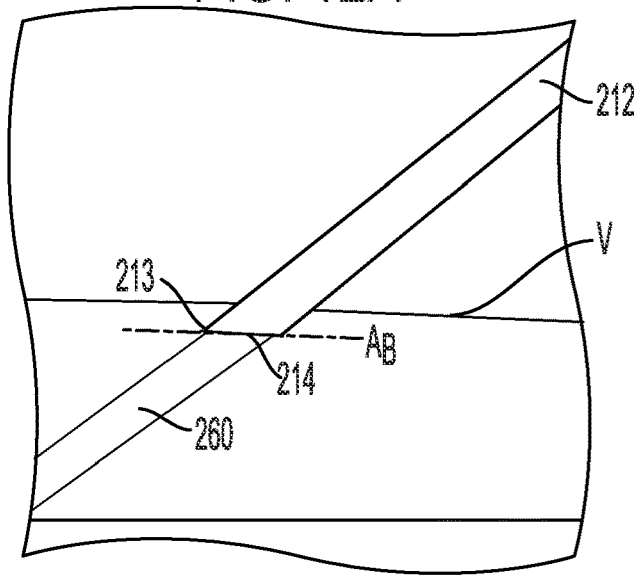
FIG. 12B is a side view of the beveled distal end in the second configuration within the vessel.
Figure 12C:
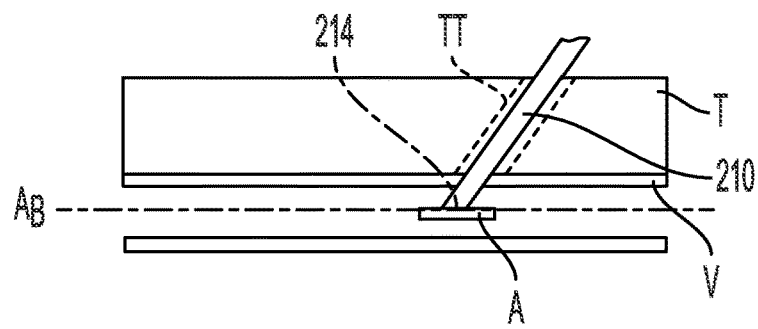
FIG. 12C is a side cross-section view of the sheath inserted through a tissue track into the vessel with the beveled distal end being in the second orientation and an anchor emanating from the beveled distal end.

Thus, as shown in FIG. 12A, the beveled distal end 214 is inserted into the vessel V (e.g., through tissue track TT as shown in FIG. 12C) such that the bisecting axis $A_B$ is oriented at an angle (e.g., not parallel) with respect to the vessel and the tip 213 penetrates a wall of the vessel V first. After insertion (e.g., after the tip 213 has passed through an opening in the wall of the vessel V), as shown in FIG. 12B, the assembly 200 is moved into the second configuration via axial displacement of the dilator 250 causing the sheath 210 to rotate such that the beveled distal end 214 is substantially parallel to the wall of the vessel V. As shown in FIG. 12C, the sheath 210 is reoriented after insertion into the vessel V through a tissue track TT defined in a tissue T such that the bisecting axis $A_B$ and therefore, the beveled distal end 214 of the sheath 210 is substantially parallel to the vessel V (e.g., a proximal wall of the vessel V). This facilitates orienting of an anchor A communicated through the channel 222 defined by the sheath 210 into the vessel V in a desired orientation, for example, substantially parallel to the wall of the vessel V.

Figure 11:
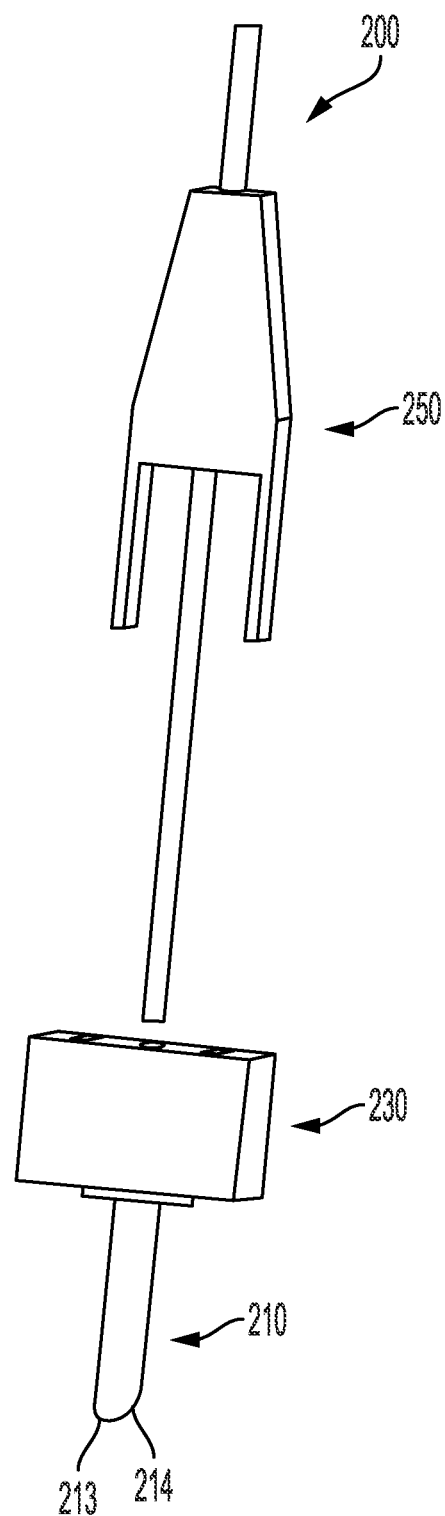
FIG. 11 is a side perspective view of the VCD assembly of FIG. 2 with the dilator being removed from the assembly after moving the assembly into the second configuration.

As shown in FIG. 11, continuing to displace the dilator 250 axially away from the housing 230 once the assembly 200 is in the second configuration, causes the dilator 250 to disengage from the sheath engagement portion 216 such that the dilator 250 can be removed from the housing 230 and eventually from the assembly 200 once the inner elongated member 260 is drawn out of the sheath 210. In some embodiments, the proximal end 219 of the helical groove 218 is structured such that axial displacement of the dilator 250 away from the sheath 210 once the assembly 200 is in the second configuration causes the engagement member 256 to disengage from the helical groove 218. For example, the proximal end 219 of the helical groove 218 may form a ramp to allow the engagement member 256 to slide out of the helical groove 218.

In other embodiments, a vertical channel may be defined on an outer surface of the sheath engagement portion 216 from a proximal edge of the sheath engagement portion 216 that is located proximate to the proximal wall 233 of the housing 230, to the proximal end 219 of the helical groove 218. Axial displacement of the dilator 250 away from the sheath 210 once the engagement member 256 is at the proximal end 219 may cause the engagement member 256 to slide into the vertical channel and ultimately out of the vertical channel such that the engagement member 256 and hence, the dilator 250 is disengaged from the sheath engagement portion 216 allowing the dilator 250 to be removed from the assembly 200.

Figure 13:
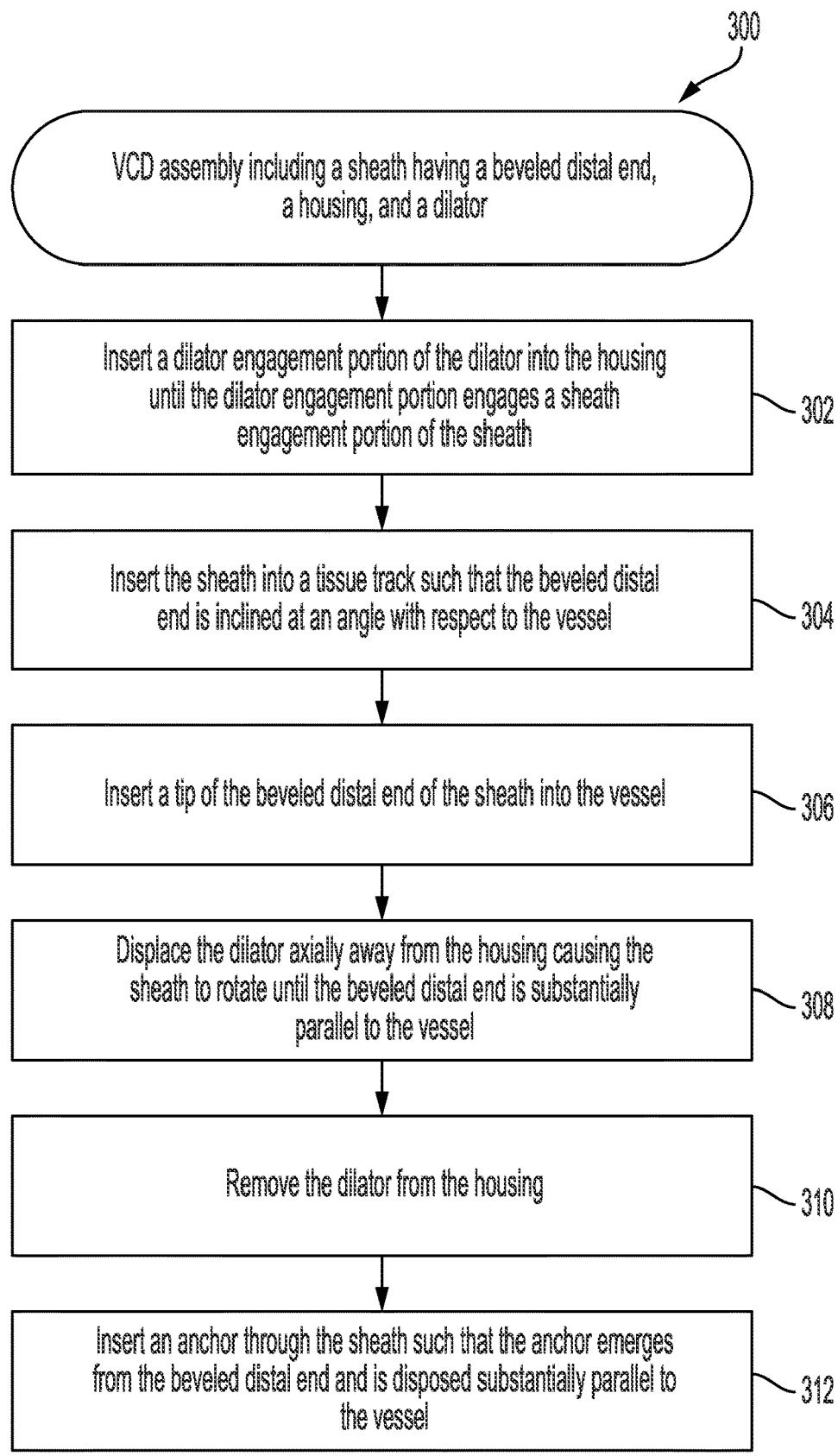
FIG. 13 is a schematic flow chart of a method for inserting a sheath of a VCD device into a vessel for performing various intravascular procedures (e.g., arteriotomies), according to an embodiment.

FIG. 13 is a schematic flow diagram of an example method 300 for operating a VCD assembly (e.g., the assembly 100, 200) that includes a sheath (e.g., the sheath 110, 210) having a sheath main body (e.g., the sheath main body 212) defining a beveled distal end (e.g., the beveled distal end 214) and a sheath mounting portion (e.g., the sheath mounting portion 220) located at a proximal end of the sheath main body. The assembly may also include a housing (e.g., the housing 130, 230), and a dilator (e.g., the dilator 150, 250) engaging the sheath through the housing. While, the method 300 is described with respect to the assembly 200, it should be appreciated that the operations of the method 300 are equally applicable to the assembly 100 or any other assembly that includes components analogous to those described herein.

In some embodiments, the method 300 includes inserting at least a portion of the dilator 250 into the housing 230, at 302, such that the dilator 250 engages the sheath 210 and moves the sheath 210 into the first configuration in which the tip 213 of the beveled distal end 214 is located on a side corresponding to a side of the vessel V in which an opening is located. For example, the dilator arms 254a/b may be inserted through the slots 234a/b, respectively and the dilator 250 displaced axially towards the housing 230 until the engagement member 256 is inserted into the helical groove 218 and rides the helical groove 218 towards the distal end 217 of the helical groove 218, thereby causing the sheath 210 to rotate and move into the first configuration. In some embodiments, the dilator 250 may include the inner elongated member 260. In such embodiments, the inner elongated member 260 is first inserted through the aperture 235 into the channel 222 defined by the sheath 210, the inner elongated member 260 facilitating axial alignment of the dilator 250 with the sheath 210. As previously described, the beveled distal end 214 is inclined at an angle with respect to a wall of the vessel V on which a procedure (e.g., hemostasis) is being performed, such that the tip 213 is located proximate to the wall of the vessel V.

At 304, the sheath 210 is inserted into the tissue track TT towards the vessel V while being in the first configuration. As previously described, the bisecting axis $A_B$ is oriented at an angle with respect to the vessel V. At 306, the tip 213 of the beveled distal end 214 is inserted through the wall of the vessel V (e.g., through the opening in the vessel) into the vessel V up to a desired depth, as previously described.

At 308, the dilator 250 is displaced axially away from the housing 230 such that the dilator 250 engages the sheath 210 and causes the sheath 210 to rotate relative to the housing 230. For example, the engagement member 256 engages the helical groove 218 causing the sheath engagement portion 216 and thereby, the sheath 210 rotates and moves into the second configuration in which the bisecting axis $A_B$ is substantially parallel to the wall of the vessel V, while the housing 230 inhibits axial displacement of the sheath 210 relative to the housing 230. In some embodiments, the sheath 210 rotates by an angle of about 180 degrees between the first configuration and the second configuration.

At 310, the dilator 250 may be removed from the assembly 200 by continuing to displace the dilator 250 axially away from the housing 230 such that the dilator 250 disengages from the sheath 210 (e.g., by disengagement of the engagement member 256 from the helical groove 218) and is subsequently removed from the housing 230, as previously described. At 312, an anchor (e.g., the anchor A such as a balloon or other structure disposed on a carrier tube) is inserted through the sheath 210 such that the anchor emerges from the beveled distal end 214 and is disposed substantially parallel to the wall of the vessel V. The anchor may be used to perform vascular hemostasis or any other vascular procedure.

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," and the like as used herein mean the joining of two members directly or indirectly to one another. Such joining may be stationary (e.g., permanent) or movable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A vascular closure device assembly, comprising:
   a sheath comprising:
      a sheath main body defining a channel therethrough, the sheath main body comprising a beveled distal end that comprises a tip and is configured to be inserted into a vessel,
      a sheath engagement portion, and
      a sheath mounting portion located at a proximal end of the sheath main body;
   a housing, wherein the sheath mounting portion is secured within the housing such that the sheath is rotatable relative to the housing, and such that the housing inhibits axial displacement of the sheath relative to the housing; and
   a dilator comprising:
      a dilator main body, and
      a dilator engagement portion extending from the dilator main body towards the sheath,
   wherein the dilator engagement portion is configured to engage the sheath engagement portion such that axial displacement of the dilator relative to the sheath causes the sheath to rotate relative to the housing;
   wherein the housing is configured to inhibit axial displacement of the sheath during rotation; and
   wherein the assembly is movable between (i) a first configuration in which the dilator engagement portion engages the sheath engagement portion at a first position, and the tip of the beveled distal end is located in a first rotational position, and (ii) a second configuration in which the dilator engagement portion engages the sheath engagement portion at a second position that is proximal the first position, and the tip of the beveled distal end is located in a second rotational position that is rotationally offset from the first rotational position.

2. The vascular closure device assembly of claim 1, wherein the second rotational position is rotationally offset from the first rotational position by about 180 degrees.

3. The vascular closure device assembly of claim 1, wherein the dilator engagement portion comprises one or more dilator arms extending from the dilator main body towards the sheath.

4. The vascular closure device assembly of claim 3, wherein:
   the housing defines one or more slots, and
   each of the one or more dilator arms extends through a corresponding slot of the one or more slots towards the sheath engagement portion.

5. The vascular closure device assembly of claim 3, wherein:
   the sheath engagement portion defines a helical groove, and
   the dilator engagement portion comprises an engagement member protruding from a corresponding dilator arm of the one or more dilator arms into the helical groove.

6. The vascular closure device assembly of claim 5, wherein a diameter of the sheath engagement portion is larger than a diameter of the sheath main body.

7. The vascular closure device assembly of claim 6, wherein the proximal end of the helical groove is structured such that, when the assembly is in the second configuration, proximal displacement of the dilator causes the engagement member to disengage from the helical groove such that the dilator can be removed from the assembly.

8. The vascular closure device assembly of claim 5, wherein:
   in the first configuration, the engagement member is located at a distal end of the helical groove,
   in the second configuration, the engagement member is located at a proximal end of the helical groove.

9. The vascular closure device assembly of claim 1, wherein the dilator further comprises:
   an inner elongated member extending axially away from the dilator main body towards the sheath and removably disposed through the channel defined through the sheath.

10. The vascular closure device assembly of claim 9, wherein the housing defines an aperture through a proximal wall of the housing, the inner elongated member being removably disposed through the aperture into the channel defined by the sheath.

11. The vascular closure device assembly of claim 1, wherein:
    the housing includes a mounting structure defined within the housing, and
    the sheath mounting portion is disposed within the mounting structure.

12. The vascular closure device assembly of claim 11, wherein:
    the sheath mounting portion is cylindrical and has a diameter that is larger than a diameter of the sheath main body; and
    the mounting structure comprises:
       a cylindrical wall extending away from a proximal wall of the housing that is proximate to the dilator towards the sheath, and
       a ledge extending radially inwards from a distal rim of the cylindrical wall;
    the sheath mounting portion has an axial length corresponding to an axial length of the cylindrical wall such that the sheath mounting portion is secured between a distal surface of the proximal wall of the housing and a proximal surface of the ledge so as to inhibit axial displacement while allowing rotation of the sheath relative to the housing.

13. A vascular closure device assembly, comprising:
    a sheath comprising:
       a sheath main body defining a channel therethrough,
       a sheath engagement portion, and
       a sheath mounting portion located at a proximal end of the sheath main body;

a housing, wherein the sheath mounting portion is secured within the housing such that the sheath is rotatable relative to the housing, and such that the housing inhibits axial displacement of the sheath relative to the housing; and a dilator comprising:
  a dilator main body,
  a dilator engagement portion extending from the dilator main body towards the sheath, and
  an inner elongated member extending axially away from the dilator main body towards the sheath and removably disposed through the channel defined through the sheath, wherein the dilator engagement portion is configured to engage the sheath engagement portion such that axial displacement of the dilator relative to the sheath causes the sheath to rotate relative to the housing;

wherein the housing is configured to inhibit axial displacement of the sheath during rotation; and wherein the housing defines an aperture through a proximal wall of the housing, the inner elongated member being removably disposed through the aperture into the channel defined by the sheath.

14. A vascular closure device assembly, comprising:
a sheath comprising:
  a sheath main body defining a channel therethrough,
  a sheath engagement portion, and
  a sheath mounting portion located at a proximal end of the sheath main body, wherein the sheath mounting portion is cylindrical and has a diameter that is larger than a diameter of the sheath main body;

a housing including a mounting structure defined within the housing, wherein the sheath mounting portion is disposed within the mounting structure and is secured within the housing such that the sheath is rotatable relative to the housing, and such that the housing inhibits axial displacement of the sheath relative to the housing; and a dilator comprising:
  a dilator main body, and
  a dilator engagement portion extending from the dilator main body towards the sheath, wherein the dilator engagement portion is configured to engage the sheath engagement portion such that axial displacement of the dilator relative to the sheath causes the sheath to rotate relative to the housing;

wherein the housing is configured to inhibit axial displacement of the sheath during rotation;

wherein the mounting structure includes a cylindrical wall extending away from a proximal wall of the housing that is proximate to the dilator towards the sheath and a ledge extending radially inwards from a distal rim of the cylindrical wall; and wherein the sheath mounting portion has an axial length corresponding to an axial length of the cylindrical wall such that the sheath mounting portion is secured between a distal surface of the proximal wall of the housing and a proximal surface of the ledge so as to inhibit axial displacement while allowing rotation of the sheath relative to the housing.

* * * * *